(12) United States Patent
Il et al.

(10) Patent No.: US 6,310,207 B1
(45) Date of Patent: Oct. 30, 2001

(54) PROCESS OF PREPARING CAMPTOTHECIN DERIVATIVES

(75) Inventors: Hong Chung Il, East Amherst, NY (US); Jung Woo Kim, Seoul (KR); Sang Joon Lee, Kunpo (KR); Soon Kil Ahn; Nam Song Choi, both of Seoul (KR); Kye Kwang Kim, Siheung (KR); Byeong Seon Jeong, Seoul (KR)

(73) Assignee: Chong Kun Dang Corp. (KR)

( * ) Notice: Subject to any disclaimer, the term of this patent is extended or adjusted under 35 U.S.C. 154(b) by 0 days.

(21) Appl. No.: 09/462,271

(22) PCT Filed: Jul. 8, 1998

(86) PCT No.: PCT/KR98/00199

§ 371 Date: Jan. 5, 2000

§ 102(e) Date: Jan. 5, 2000

(87) PCT Pub. No.: WO99/02530

PCT Pub. Date: Jan. 21, 1999

(30) Foreign Application Priority Data

Jul. 9, 1997 (KR) .................................................. 97-31710

(51) Int. Cl.[7] ...................... C07D 487/14; C07D 487/22
(52) U.S. Cl. ................................................ 546/41; 546/44
(58) Field of Search .......................................... 546/44, 41

(56) References Cited

FOREIGN PATENT DOCUMENTS

| | | |
|---|---|---|
| 0 296 597 A2 | 12/1988 | (EP) . |
| 0 471 358 A1 | 2/1992 | (EP) . |
| 0 495 432 A1 | 7/1992 | (EP) . |
| WO 96/21666 | 7/1996 | (WO) . |

OTHER PUBLICATIONS

Sawada, S. et al., "Chemical Modification of an Antitumor Alkaloid Camptothecin: Synthesis and Antitumor Activity of 7–C–Substituted Camptothecins," *Chem Pharm. Bull.*, 39:274–80 (1991).

Wall, M.E. et al., "Plant Antitumor Agents. I. The Isolation and Structure of Camptothecin, a Novel Alkaloidal Leukemia and Tumor Inhibitor from *Camptotheca acuminata*," *J. Am. Chem. Soc*, 88:3888–90 (1996).

*Primary Examiner*—Alan L. Rotman
(74) *Attorney, Agent, or Firm*—Heslin Rothenberg Farley & Mesiti P.C.

(57) ABSTRACT

A process of preparing camptothecin derivatives of formula 1 is disclosed

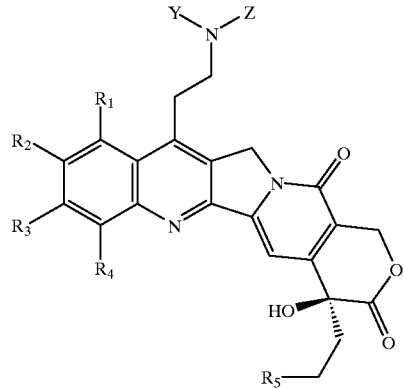

8 Claims, No Drawings

PROCESS OF PREPARING CAMPTOTHECIN DERIVATIVES

PRIOR FOREIGN APPLICATIONS

This application is a 35 USC §371 filing of PCT/KR98/00199, filed Jul. 8, 1998 and claims priority from Korean Patent Application Number 1997/31710, filed Jul. 9, 1997.

TECHNICAL FIELD

This invention relates to a process of manufacturing a camptothecin derivative expressed by the following general formula 1, or a pharmaceutically acceptable salt thereof:

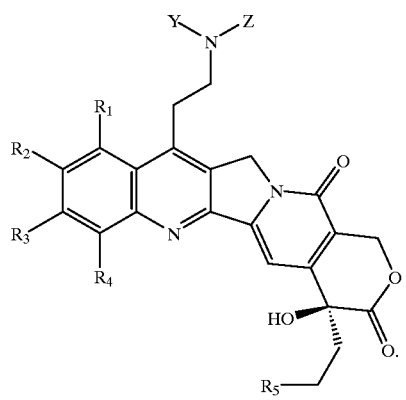

wherein
- Y and Z are the same or different and each represents a hydrogen atom, an $C_1$~$C_6$ alkyl group, a $C_1$~$C_3$ hydroxyalkyl group, or a general protecting group of amine such as benzyloxycarbonyl, benzyl, etc.;
- $R_1$ is a hydrogen atom, an $C_1$~$C_6$ alkyl group, or a hydroxy group;
- $R_2$ and $R_3$ are the same or different and each represents a hydrogen atom or a hydroxy group, or they may be attached together to form a cyclic moiety, which is a methylenedioxy or an ethylenedioxy group;
- $R_4$ is a hydrogen atom or an $C_1$~$C_6$ alkyl group; and
- $R_5$ is hydrogen, hydroxy, fluoro, chloro, bromo, iodo or amine.

BACKGROUND ART

Since the first isolation of camptothecin from the wood and bark of *Camptotheca acuminata* by Wall and co-workers [M. E. Wall et al., *J. Am. Chem. Soc.*, 88, 3888 (1966)], there had been many approaches to synthesize camptothecin. However, the development of camptothecin as an effective antineoplastic agent was unsuccessful due to its severe toxicity in the clinical trial in 1970. Thereafter, Liu et a reported in 1985 that camptothecin had a specific mode of action to inhibit topoisomerase I. Thus, considerable interest has focused on this compound.

Recently, various studies for the development of camptothecin derivatives have been proposed in order to reduce the toxicity of camptothecin and to further enhance its antineoplastic activities. Among these related studies, the clinical trial of CPT-11 (irinotecan) synthesized by Yakurt-Honsha Co. of Japan in 1986 showed that it exhibited excellent antineoplastic activities with less toxicity (Japanese Patent Laid Open Publication No. 64-61482) and followed by other pharmaceutical companies such as Smithkline Beecham (topotecan) and Glaxo (MDO-camptothecin and 9-amino camptothecin). Among them, CPT-11 and topotecan are launched.

On the other hand, the present inventors have reported the 7-aminoethyl camptothecin derivatives and manufacturing process thereof through the total synthesis, which have strong antitumor activity, weak toxicity, and broad safe region, in Korean Patent Application No. 95-269 and 96-248.

The above invention produces camptothecin derivatives that have strong antitumor activity. However, the procedure of manufacturing those is complex since the total synthesis is adopted and since intermediate material used is a new one. Consequently, there has been a strong need to develop a simple and convenient manufacturing process of camptothecin derivatives for mass production.

Accordingly, the inventors et al. have studied a convenient process by which camptothecin derivatives having excellent activities can be manufactured from a compound of general formula 2 such as (S)-7-methylcamptothecin [S. Sawada et al., *Chem. Pharm. Bull.*, 39 (1991) 2574~2580]. Thus, the present invention has been completed.

DISCLOSURE OF THE INVENTION

A process of manufacturing a camptothecin derivative or a pharmaceutically acceptable salt thereof is described in more detail as set forth hereunder, in accordance with the practice of this invention.

The process of manufacturing a camptothecin derivative or a pharmaceutically acceptable salt thereof, according to the present invention, is to produce the compound of general formula 1 through Mannich Reaction, that is, a compound of general formula 2 is reacted with an amine or salt thereof and with a formaldehyde source in the presence of acid (Scheme 1).

Scheme I

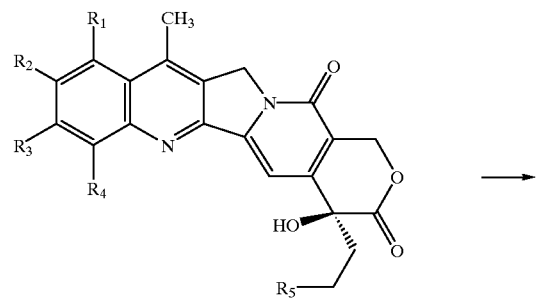

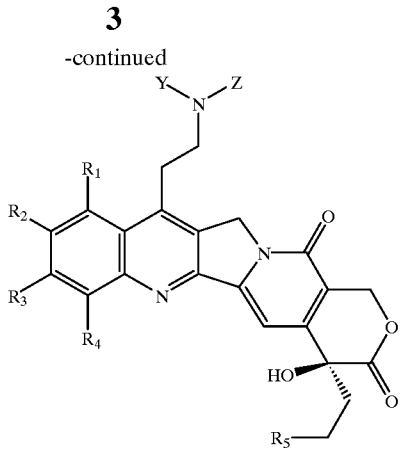

wherein
- Y and Z are the same or different and each represents a hydrogen atom, an $C_1$~$C_6$ alkyl group, a $C_1$~$C_3$ hydroxyalkyl group, or a general protecting group of amine such as benzyloxycarbonyl, benzyl, etc.;
- $R_1$ is a hydrogen atom, an $C_1$~$C_6$ alkyl group, or a hydroxy group;
- $R_2$ and $R_3$ are the same or different and each represents a hydrogen atom or a hydroxy group, or they may be attached together to form a cyclic moiety, which is a methylenedioxy or an ethylenedioxy group;
- $R_4$ is a hydrogen atom or an $C_1$~$C_6$ alkyl group; and
- $R_5$ is hydrogen, hydroxy, fluoro, chloro, bromo, iodo or amine.

Preferably, $R_1$, $R_2$, $R_3$, $R_4$, $R_5$ and Y represent hydrogen atoms, and Z is isopropyl.

Examples of the said formaldehyde source comprise formalin solution, paraformaldehyde, trioxane, dimethyl sulfoxide, etc.

Examples of the said amine comprise primary or secondary amines such as methyl amine, ethyl amine, propyl amine, isopropyl amine, butyl amine, pentyl amine, hexyl amine, benzyl amine, isopropylbenzyl amine, dimethyl amine, diethyl amine, benzyloxycarbonyl amine, hydroxymethyl amine, hydroxyethyl amine, hydroxypropyl amine and the like.

In this reaction, examples of a reaction solvent comprise water, methanol, ethanol, dioxane, acetic acid, dimethylformamide, dimethyl sulfoxide and the like. Examples of the said acid comprise hydrochloric acid, sulfuric acid, acetic acid, phosphoric acid, p-toluenesulfonic acid, methanesulfonic acid, trifluoromethanesulfonic acid, boron trifluoride, tin chloride and the like. And the reaction temperature is 20~150° C.

According to the present invention, pharmaceutically acceptable salts of compounds represented with general formula 1 are inorganic acid salts such as hydrochloride, sulfate, phosphate, etc., or organic acid salts such as p-toluenesulfonate, acetate, methanesulfonate, trifluoromethanesulfonate, etc.

BEST MODE FOR CARRYING OUT THE INVENTION

This invention is explained in more detail by the following examples but the claims are not limited to these examples.

EXAMPLE 1

(S)-7-[2-(N-isopropylamino)ethyl]camptothecin Hydrochloride (S)-7-methylcamptothecin (8 g, 0.0221 mol), isopropylamine (3.91 g, 0.0662 mol) and c-HCl (6.93 ml, 0.0684 mol) were added to dimethyl sulfoxide (80 ml). The reaction mixture was stirred at 140° C. for one hour, and then cooled to room temperature. And the reaction solvent was removed by distillation under reduced pressure and the residue, so obtained, was purified by flash column chromatography with (methylene chloride: methanol=10:1) to give the desired product (6.75 g, 65%) as pale yellow solid.

$^1$H NMR (DMSO-$d_6$, 400 MHz) δ: 9.29 (brs, 1H), 8.39 (d, 1H, J=8.3 Hz), 8.13 (d, 1H, J=8.3 Hz), 7.83 (t, 1H, J=7.1 Hz), 7.72 (t, 1H, J=7.1 Hz), 7.29 (s, 1H), 6.52 (s, 1H), 5.43 (s, 2H), 5.37 (s, 2H), 3.64~3.60 (m, 2H), 3.45~3.34 (m, 1H), 3.20~3.14 (m, 2H), 1.92~1.82 (m, 2H), 1.27 (d, 6H, J=6.4 Hz), 0.87 (t, 3H, J=8.0 Hz)

EXAMPLE 2

(S)-7-[2-(N-isopropylamino)ethyl]camptothecin Hydrochloride (S)-7-methylcamptothecin (8 g, 0.0221 mol) and isopropylamine (3.91 g, 0.0662 mol) were added orderly in a mixed solution of formalin solution (37%, 9.73 ml, 0.12 mol) and c-HCl (6.93 ml, 0.0684 mol). The reaction mixture was stirred under reflux for 12 hours, and then cooled to room temperature. The reaction solvent was removed by distillation under reduced pressure and the residue, so obtained, was purified by flash column chromatography with (methylenechloride:methanol=10:1) to give the desired product (6.23 g, 60%) as pale yellow solid. The analysis data of the product is the same as example 1.

EXAMPLE 3

(S)-7-[2-(N-isopropylamino)ethyl]camptothecin Hydrochloride (S)-7-methylcamptothecin (8 g, 0.0221 mol), isopropylamine (3.91 g, 0.0662 mol) and paraformaldehyde (5 g) were added orderly in a mixed solution of ethanol (30 ml), water (30 ml) and c-HCl (6.93 ml, 0.0684 mol). Then, the reaction mixture was stirred under reflux for 20 hours, and then cooled to room temperature. The reaction solvent was removed by distillation under reduced pressure and the residue, so obtained, was purified by flash column chromatography with (methylene chloride:methanol=10:1) to give the desired product (6.35 g, 61.1%) as pale yellow solid. The analysis data of the product is the same as example 1.

EXAMPLE 4

(S)-7-[2-(N-propylamino)ethyl]camptothecin Hydrochloride

The same procedure as in example 1 was applied to propylamine (496 mg, 0.0084 mol) and (S)-7-methyl camptothecin (1.005 g, 0.0028 mol) to give the desired product (677 mg, 52%) as pale yellow solid.

$^1$H-NMR (DMSO-$d_6$) δ: 9.26 (brs, 1H), 8.43~7.7 (m, 4H), 7.3 (s, 1H), 6.48 (s, 1H), 5.42 (s, 2H), 5.29 (s, 2H), 3.64~3.37 (m, 2H), 3.2~3.11 (m, 4H), 1.92~1.82 (m, 2H), 1.27~1.11 (m, 8H), 0.88 (t, 3H, J=7.2 Hz), 0.81 (t, 3H, J=7.3 Hz)

EXAMPLE 5

(S)-7-[2-(N-isopropylamino)ethyl]-10,11-Methylenedioxycamptothecin Hydrochloride The same procedure as in example 1 was applied to (S)-7-methyl-10,11-methylenedioxycamptothecin (1 g, 0.00248 mol) and isopropylamine (440 mg, 0.00744 mol) to give the desired product (540 mg, 48%) as pale yellow solid.

$^1$H NMR (DMSO-d$_6$) δ: 9.21 (brs, 1H), 7.6 (s, 1H), 7.4 (s, 1H), 7.21 (s, 1H), 6.28 (s, 2H), 5.4 (s, 2H), 5.32 (s, 2H), 3.64~3.60 (m, 2H), 3.45~3.34(m, 1H), 3.19~3.10 (m, 2H), 1.92~1.81 (m, 2H), 1.27 (d, 6H, J=7.1 Hz), 0.88(t, 3H, J=7.2 Hz)

EXAMPLE 6

(S)-7-[2-(N-isopropylamino)ethyl]-10,11-ethlenedioxycamptothecin Hydrochloride

The same procedure as in example 2 was applied to (S)-7-methyl-10,11-methylenedioxycamptothecin (1 g, 0.00248 mol) and isopropylamine (440 mg, 0.00744 mol) to give the desired product (600 mg, 53%) as pale yellow solid. The analysis data of the product is the the same as example 5.

EXAMPLE 7

(S)-7-[2-(N-isopropylamino)ethyl]-10,11-ethylenedioxycamptothecin Hydrochloride

The same procedure as in example 3 was applied to (S)-7-ethyl-10,11-methylenedioxycamptothecin (1 g, 0.00248 mol) and isopropylamine (440 mg, 0.00744 mol) to give the desired product (565 mg, 51%) as pale yellow solid. The analysis data of the product is the same as example 5.

EXAMPLE 8

(S)-7-[2-(N-isopropylamino)ethyl]-10,11-ethylenedioxycamptothecin Hydrochloride

The same procedure as in example 1 was applied to (S)-7-methyl-10,11-ethylenedioxycamptothecin (1 g, 0.00239 mol) and isopropylamine (440 mg, 0.00744 mol) to give the desired product (703 mg, 56%) as pale yellow solid.

$^1$H NMR (DMSO-d$_6$) δ: 9.20 (brs, 1H), 7.58 (s, 1H), 7.4 (s, 1H), 7.23 (s, 1H), 6.31 (m, 2H), 5.8 (m, 2H), 5.4 (s, 2H), 5.32 (s, 2H), 3.61~3.3 (m, 2H), 3.17~3.11(m, 3H), 1.96~1.84 (m, 2H), 1.27 (d, 6H, J=7.5 Hz), 0.92(t, 3H, J=6.8 Hz)

EXAMPLE 9

(S)-7-[2-(N-isopropylamino)ethyl]-10,11-ethylenedioxycamptothecin Hydrochloride

The same procedure as in example 2 was applied to (S)-7-methyl-10,11-ethylenedioxycamptothecin (1 g, 0.00239 mol) and isopropylamine (440 mg, 0.00744 mol) to give the desired product (579 mg, 46%) as pale yellow solid. The analysis data of the product is the same as example 8.

EXAMPLE 10

(S)-7-[2-(N-isopropylamino)ethyl]-10,11-ethylenedioxycamptothecin Hydrochloride

The same procedure as in example 3 was applied to (S)-7-methyl-10,11-ethylenedioxycamptothecin (1 g, 0.00239 mol) and isopropylamine (440 mg, 0.00744 mol) to give the desired product (668 mg, 53%) as pale yellow solid. The analysis data of the product is the same as example 8.

EXAMPLE 11

(S)-7-[2-(N-propylamino)ethyl]-10,11-methylenedioxycamptothecin hydrochloride

The same procedure as in example 1 was applied to (S)-7-methyl-10,11-methylenedioxycamptothecin (1 g, 0.00248 mol) and propylamine (440 mg, 0.00744 mol) to give the desired product (466 mg, 42%) as pale yellow solid.

$^1$H NMR (DMSO-d$_6$) δ: 7.6 (s, 1H), 7.38 (s, 1H), 7.21 (s, 1H), 6.26 (s, 2H), 5.4 (s, 2H), 5.29 (s, 2H), 3.56~3.31 (m, 2H), 3.18~3.03 (m, 4H), 1.91~1.81 (m, 2H), 1.29~1.04 (m, 8H), 0.87 (t, 3H, J=6.8 Hz), 0.74 (t, 3H, J=7.1 Hz)

EXAMPLE 12

(S)-7-[2-(N-propylamino)ethyl]-10,11-ethylenedioxycamptothecin Hydrochloride

The same procedure as in example 1 was applied to (S)-7-ethyl-10,11-ethylenedioxycamptothecin (1 g, 0.00239 mol) and propylamine (440 mg, 0.00744 mol) to give the desired product (575 mg, 46%) as pale yellow solid.

$^1$H NMR (DMSO-d$_6$) δ: 7.6 (s, 1H), 7.36 (s, 1H), 7.20 (s, 1H), 6.26 (s, 2H), 5.81 (s, 2H), 5.41 (s, 2H), 5.28 (s, 2H), 3.52~3.41 (m, 2H), 3.16~3.01 (m, 4H), 1.93~1.79 (m, 2H), 1.28~1.02 (m, 8H), 0.88 (t, 3H, J=7.1 Hz), 0.78 (t, 3H, J=7.1 Hz)

EXAMPLE 13

(S)-7-[2-(N-isopropylbenzylamino)ethyl]camptothecin Hydrochloride (S)-7-methylcamptothecin (8 g, 0.0221 mol), isopropylbenzylamine (9.88 g, 0.0662 mol) and c-HCl (6.93 ml, 0.0684 mol) were added to dimethyl sulfoxide (80 ml). Then, the same procedure as in example 1 was performed to give the desired product (9.27 g, 75%) as pale yellow solid.

$^1$H NMR (DMSO-d$_6$, 400MHz) δ: 8.38 (d, 1H, J=8.5 Hz), 8.13(d, 1H, J=8.5 Hz), 7.86 (dd, 1H, J=8.5, 8.0 Hz), 7.74 (dd, 1H, J=8.5, 8.0 Hz), 7.52~7.31 (m, 5H), 7.29 (s, 1H), 6.52 (s, 1H), 5.43 (s, 2H), 5.35 (s, 2H), 3.66~3.59 (m, 2H), 3.54 (s, 2H), 3.45~3.34 (m, 1H), 3.21~3.16 (m, 2H), 1.92~1.82 (m, 2H), 1.26 (d, 6H, J=6.4 Hz), 0.88 (t, 3H, J=8.0Hz)

EXAMPLE 14

(S)-7-[2-(N-isopropylamino)ethyl]camptothecin Hydrochlorid

Pd-C (10%, 500 mg), 4.4% formic acid (10 ml) and methanol (100 ml) were added to (S)-7-[2-(N-isopropyl benzylamino)ethyl]camptothecin hydrochloride (5 g, 0.0089 mol) and the reaction mixture was stirred at room temperature for 18 hours. Then, the reaction solution was filtered and the filtrate, so obtained, was distilled under reduced pressure. The residue, so obtained, was purified by flash column chromatography (methylenechloride:methanol=10:1) to give the desired product (3.6 g, 86%) as pale yellow solid. The analysis data of the product is the same as example 1.

The present invention relates to a process of manufacturing camptothecin derivatives or pharmaceutically acceptable salts thereof. Especially, 7-substituted camptothecin derivatives that have excellent antineoplastic activities can be manufactured easily and economically through the said process.

What is claimed is:
1. A process of preparing a compound of formula 1, or a salt thereof, the process comprising:
(a) reacting a compound of formula 2

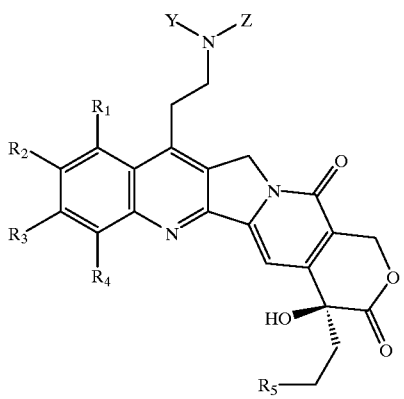

1

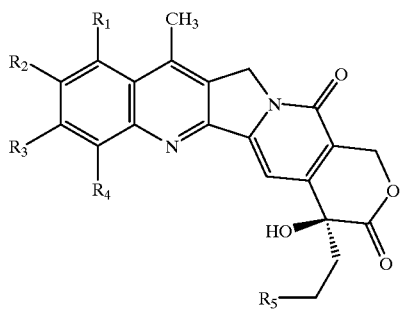

2 wherein
Y and Z are independently chosen from —H, a $C_1$ to $C_6$ alkyl group, a $C_1$ to $C_3$ hydroxyalkyl group, and an amine protecting group;
$R_1$ is selected from —H, a $C_1$ to $C_6$ alkyl group and a hydroxy group;
$R_2$ and $R_3$ are independently selected from —H and hydroxy, or taken together form a methylenedioxy or ethylenedioxy group;
$R_4$ is selected from —H and a $C_1$ to $C_6$ alkyl group; and
$R_5$ is selected from —H, hydroxy, halogen and amine with an amine, or salt thereof, and a source of formaldehyde in the presence of an acid; and
(b) obtaining a compound of formula 1, or a salt thereof.

2. A process according to claim 1, wherein $R_1$, $R_2$, $R_3$, $R_4$, $R_5$ and Y are each —H and Z is isopropyl.

3. A process according to claim 1, wherein the source of formaldehyde is selected from formalin solution, paraformaldehyde and trioxane.

4. A process according to claim 1, wherein the amine is selected from methyl amine, ethyl amine, propyl amine, isopropyl amine, butyl amine, pentyl amine, hexyl amine, benzyl amine, isopropylbenzyl amine, dimethyl amine, diethyl amine, benzyloxycarbonyl amine, hydroxymethyl amine, hydroxyethyl amine and hydroxypropyl amine.

5. A process according to claim 1, wherein a reaction solvent is selected from water, methanol, ethanol, dioxane, acetic acid, dimethylformamide and dimethyl sulfoxide; the acid is selected from hydrochloric acid, sulfuric acid, acetic acid, phosphoric acid, p-toluenesulfonic acid, methanesulfonic acid, trifluoromethanesulfonic acid, boron trifluoride and tin chloride; and the reaction temperature is 20–150° C.

6. A process according to claim 2, wherein the source of formaldehyde is selected from formalin solution, paraformaldehyde and trioxane.

7. A process according to claim 2, wherein the amine is chosen from methyl amine, ethyl amine, propyl amine, isopropyl amine, butyl amine, pentyl amine, hexyl amine, benzyl amine, isopropylbenzyl amine, dimethyl amine, diethyl amine, benzyloxycarbonyl amine, hydroxymethyl amine, hydroxyethyl amine and hydroxypropyl amine.

8. A process according to claim 2, wherein a reaction solvent is selected from water, methanol, ethanol, dioxane, acetic acid, dimethylformamide and dimethyl sulfoxide; the acid is chosen from hydrochloric acid, sulfuric acid, acetic acid, phosphoric acid, p-toluenesulfonic acid, methanesulfonic acid, trifluoromethanesulfonic acid, boron trifluoride and tin chloride; and the reaction temperature is 20–150° C.

* * * * *